United States Patent [19]

Lhonoré et al.

[11] 4,313,009
[45] Jan. 26, 1982

[54] PROCESS AND INSTALLATION FOR MAKING NITROPARAFFINS BY NITRATION OF HYDROCARBONS IN THE GASEOUS PHASE

[75] Inventors: Pierre Lhonoré, Douai; Jacques Quibel, Maisons Laffitte; Bernard Jacquinot, Douai, all of France

[73] Assignee: Societe Chimique de la Grande Paroisse, Azote et Produits Chimiques, Paris, France

[21] Appl. No.: 132,539

[22] Filed: Mar. 21, 1980

[30] Foreign Application Priority Data

Apr. 10, 1979 [FR] France ............................ 79 08997

[51] Int. Cl.³ ..................... C07C 76/02; C07C 79/04
[52] U.S. Cl. .................................. 568/947; 568/948; 422/168; 422/188; 422/234; 422/235
[58] Field of Search ................................ 568/947, 948

[56] References Cited

U.S. PATENT DOCUMENTS

| | | | |
|---|---|---|---|
| Re. 21,657 | 12/1940 | Martin et al. | 568/947 |
| 1,967,667 | 7/1934 | Hass et al. | 568/947 |
| 2,260,258 | 10/1941 | Martin | 568/947 |
| 2,309,845 | 2/1943 | Hodge | 568/947 |
| 2,327,964 | 8/1943 | Hodge | 568/947 |
| 2,332,491 | 10/1943 | Senkus | 568/947 |
| 2,346,441 | 4/1944 | Lippincott | 568/947 |
| 2,491,919 | 12/1949 | Egly | 568/947 |
| 2,609,401 | 9/1952 | Haas et al. | 568/947 |
| 3,869,253 | 3/1975 | Lhonore et al. | 568/947 |
| 4,260,838 | 4/1981 | Lhonore et al. | 568/947 |

FOREIGN PATENT DOCUMENTS

| | | | |
|---|---|---|---|
| 11553 | 5/1980 | European Pat. Off. | 568/947 |
| 2158681 | 6/1973 | France | 568/947 |

*Primary Examiner*—Teddy S. Gron
*Attorney, Agent, or Firm*—Browdy and Neimark

[57] ABSTRACT

A process making nitroparaffins comprises a nitration reaction in the gaseous phase, under pressure, in a closed loop with recycling of the products that have not reacted, with continuous deconcentration purge and continuous input of hydrocarbon and nitrating agent. The process is applicable to nitration of saturated hydrocarbon less than $C_5$, above or in mixture.

12 Claims, 1 Drawing Figure

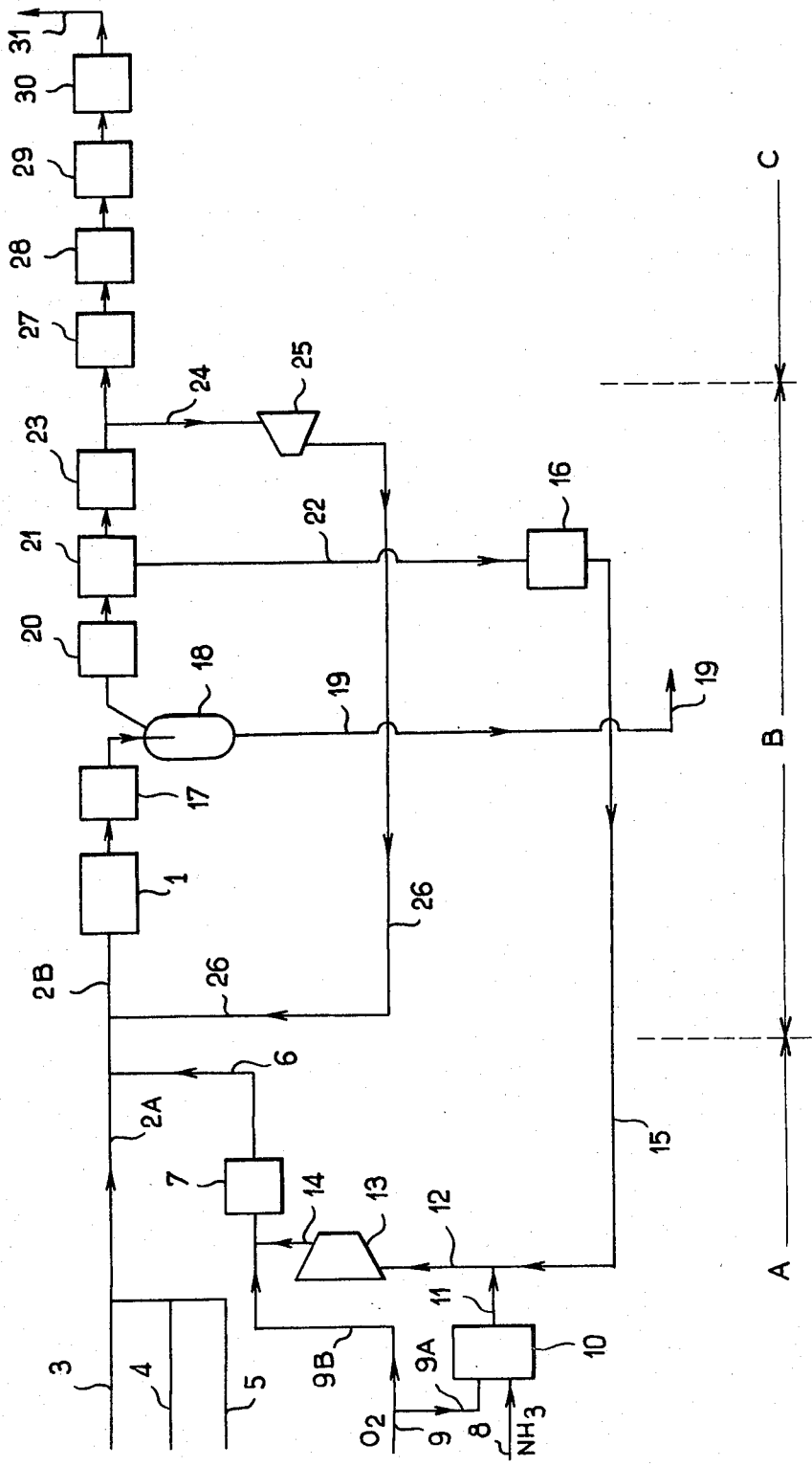

PROCESS AND INSTALLATION FOR MAKING NITROPARAFFINS BY NITRATION OF HYDROCARBONS IN THE GASEOUS PHASE

FIELD OF INVENTION

This invention relates to a process of making nitroparaffins by nitration in homogeneous gaseous phase of a saturated hydrocarbon having less than five carbons, using a nitrating agent, and an installation for effecting this nitration.

BACKGROUND OF INVENTION

Various nitration processes are already known, particularly of ethane, propane and their mixtures in the gaseous phase as described in the copending U.S. Pat. application Ser. No. 25,594, U.S. Pat. No. 4,260,838, and Ser. No. 94,153. According to these processes, the quantitative ratios of the various constituents of the reaction mixture, the reaction contact times, temperatures, and reaction pressures are selected and controlled so that nitration of the hydrocarbons or their mixtures is carried out in the homogeneous gaseous phase, and as a function of the expected range of nitroparaffin products.

One of the present industrial problems lies in the search for means making it possible to obtain a percentage of different nitroparaffins suited to market demands. For example, it has been found that 2-nitropropane is presently not the most usable nitroparaffin; rather, requirements for nitromethane have grown as a function of the growing uses of this product. However, market demands change, and flexibility in the nature of the product produced, heretofore not readily feasible, is highly desired. While an increase in the reaction temperature results in a proportionally higher production of nitromethane, this undesirably requires a higher cost as a result of a more thorough degradation of the hydrocarbons into oxidized products. And, of course, higher temperatures require greater energy expenditures.

SUMMARY OF INVENTION

A process has been found that mitigates the aforementioned drawback in great part while making possible the production of selected products meeting market demands and at an advantageous cost for the nitroparaffins made.

According to the process of the invention, a closed-loop nitration reaction is used under pressure with separation of the reaction effluents into a gaseous phase and a liquid phase; the liquid phase containing particularly the nitroparaffins produced is extracted and is treated to recover the nitroparaffins; the gaseous phase is subjected to a primary purification treatment, and the major portion of the so purified gaseous phase is then recycled in the nitration loop and is heated under the pressure prevalent in the loop; a continuous deconcentration purge is made of the smaller portion of the purified gaseous phase which is purified and from which are removed hydrocarbons and nitrogen oxides; and there are continuously added hydrocarbon, on the one hand, and a nitrating agent, on the other hand.

The pressure in the nitration loop is between 1 bar and 30 bars, and preferably 8 and 20 bars. The nitrating agent is selected from nitrogen peroxide, nitric acid, alone or in mixture, or any agent carrying an easily transferable NO or $NO_2$ group.

To limit the phenomenon of thorough degradation of the hydrocarbon into oxidized products, it is advantageous to keep the reaction temperature at a determined level with careful control of the temperature elevation curve during nitration, by performing the nitration in a reactor suited to good heat exchange and making it possible to perform the nitration with a regular, progressive heat regime, with an output temperature of the effluents at the end of nitration below 400° C.

The process is particularly suitable for making, in a homogeneous gaseous phase, nitroparaffins from saturated hydrocarbons below $C_5$, alone or in mixture, particularly ethane and propane. The nitration can be performed in the presence of oxygen in the form of air, superoxygenated air or pure oxygen. To direct the synthesis toward a given range of nitroparaffins, it is often advantageous to perform the nitration in the presence of an active agent carrying an easily transferable NO or $NO_2$ group, such as 2-nitropropane and nitroethane alone or in mixture, which can be recycling products of the reaction; it is also possible to operate in the presence of adjuvants, such as ethanal.

The variations of the active agent/nitrating agent molar ratio give great flexibility of adaptation of the process to market demands. And this ratio is adjusted as a function of the expected range of nitroparaffins.

Nitration in the presence of one or more gases that are inert in regard to the reaction and reaction products can be effected to help facilitate recovery of residual hydrocarbon at the nitration output. This inert gas can be selected from nitrogen, carbon monoxide, carbon dioxide, hydrogen, methane, argon or a mixture of these gases.

The reaction temperature within the limits indicated above, assuring nitration in the homogeneous vapor phase for a given pressure, is further selected as a function of the hydrocarbon or mixture of hydrocarbons treated, of recycled adjuvants, and of the ratios of the constituents of the mixture of reagents at the input of the reaction zone, to obtain a mixture of nitroparaffin of a predetermined range.

The gases leaving the nitration reaction zone are cooled as quickly as possible and at a temperature as low as possible but compatible with the pressure, while avoiding any condensation of the hydrocarbon that has not reacted. After this quenching, two phases are obtained: a liquid phase and a gaseous phase. The liquid phase, which is withdrawn from the loop, contains particularly nitroparaffins which are subjected to a series of purification treatments before distillation.

The gaseous phase is subjected to a first treatment of washing with water, which assures elimination of oxidized products including aldehydes, ketones and various nitride products. It is then subjected to washing with a solution of metal sulfate selected from the following metal sulfates: iron $Fe^{++}$, cobalt $Co^{++}$, copper $Cu^+$, for absorption of nitrogen monoxide. The major part of this purified gaseous phase is then recycled to the nitration loop after reheating and recompression to the nitration pressure.

According to the process, there are extracted from the nitration loop the gaseous products that cannot be recycled without having the loop enriched with undesirable gases. A continuous deconcentration purge makes possible the elimination of carbon monoxide, carbon dioxide and nitrogen introduced to or formed in the reaction. To reduce to a minimum the losses of quantity of potential nitroparaffin production, this purge represents 10 to 20% of the amount of gas of the nitration loop. This part of the gaseous phase constituting the continuous deconcentration purge is subjected, under pressure, to first a secondary purification comprising a treatment for the recovery of hydrocarbons using an aliphatic solvent having a molecular mass of 100 to 200, such as a saturated hydrocarbon above $C_6$; and then next to a washing treatment with a solution containing the above-cited metal sulfates to recover nitrogen monoxide. The solutions that have been used for these absorbing washings are regenerated and the hydrocarbons, on the one hand, and the nitrogen monoxide, on the other hand, after oxidation treatment to form nitrogen peroxide, are recycled.

As oxidizing agent, in whose presence the nitration is performed, air or oxygen can be used. However, oxygen leads to the easiest and most well-rounded solution from the technical viewpoint. Actually, the presence of considerable amounts of nitrogen either leads to appreciable losses of hydrocarbons entrained with the gaseous purge or requires a hydrocarbon recovery system that can be complex. The availability of oxygen easily makes it possible to produce nitrogen peroxide consumed in the nitration reaction and further to reoxidize the nitrogen monoxide recovered and regenerated after nitration.

The nitrogen monoxide corresponding to the nitrogen peroxide consumed in the nitration reaction is made by oxidation of ammonia by oxygen in the presence of steam; after condensation and washing, the nitrogen monoxide that has been formed is added to the nitrogen monoxide extracted and recycled from the main nitration loop, such extracted and recycled nitrogen monoxide having been obtained by suitable washing of the gaseous phase by the afore-mentioned metal sulfates followed by regeneration. All the nitrogen monoxide is then oxidized under the pressure of the nitration loop with oxygen in concentrated phase in a reactor capable of controlling the reaction while avoiding any racing of the reaction, and heat from this very exothermic reaction is recovered.

It is advantageous to perform oxidation of the ammonia with oxygen in the presence of steam catalyzed on platinum gauze at a temperature between 780° and 900° C., preferably between 820° and 850° C. This type of oxidation produces nitrogen monoxide with an average yield of 80–90% based on the nitrogen. After condensation of the water, the nitrogen monoxide is compressed to the pressure of the loop and is oxidized in the presence of excess oxygen to supply the loop with additional nitrogen peroxide at the same time as the oxygen. This oxidation of the nitrogen monoxide is nitrogen peroxide is performed at a temperature between 750° C. and ambient temperature, and preferably between 550° and 100° C. in a reactor capable of rapidly eliminating the reaction heat. This reactor can be a fast action boiler having multiple oxygen inlets into the nitrogen monoxide.

BRIEF DESCRIPTION OF DRAWING

A nitroparaffin-making installation suited for using the process of the invention is shown in the FIGURE of the accompanying drawing.

DETAILED DESCRIPTION OF EMBODIMENT

The installation shown comprises a main nitration loop B comprising a nitration reactor 1; a reaction heat thermal recovery unit or quencher 17; a separator 18 for withdrawal of the condensed products after nitration, removed by a pipe 19 from the gaseous effluents, such separator 18 being located in the nitration line between the thermal recovery unit 17 and devices 20 and 23 used for purification of effluent gases and a device 21 for recovery of the nitrogen monoxide; and a circuit 24 for extraction of the major part of effluent gaseous phase after purification and freed of nitrogen monoxide, in which is inserted a booster compressor 25 which compresses the gases that have not reacted to the loop pressure and sends them back by pipes 26 and then 2B to the reactor 1.

The installation comprises a continuous purge line in which are placed a device 27 for washing the purge gas with an aliphatic solvent, a device 28 for recovery of the hydrocarbon that has not reacted and which will be recycled and reintroduced to the installation by a pipe 3, a device 29 for washing the gases with a metal sulfate solution, and a device for recovery of the nitrogen monoxide; after decompression, the gases leaving the circuit 31 can be flared.

The installation also comprises a system A for feeding the various constituents of the reaction mixture; the hydrocarbon is introduced by pipe 3, the adjuvants by pipe 4 and the recycled products by pipe 5, these constituents being united in pipe 2A from where they pass into pipe 2B and then into the reactor 1. The installation further comprises a circuit for the recycling of the nitrogen monoxide recovered from the main loop in device 21, this recovered monoxide being carried through a pipe 22 to a regeneration device 16 and then by pipes 15 and 12 to a booster compressor 13. The nitrogen monoxide compressed to the pressure of the main loop is sent through a pile 14 and oxidized in oxidation reactor 7 and the nitrogen peroxide formed is reintroduced into the main nitration loop by pipe 6, and then by pipe 2B into the nitration reactor 1.

Optionally, the installation can further include an ammonia oxidation reactor 10 in which the ammonia and oxygen are respectively introduced by pipes 8 and 9A, the so-formed nitrogen monoxide is then passed from the reactor 10 through a pipe 11 and then added to the regenerated nitrogen monoxide passing through the pipe 12. The oxygen present in the nitration reactor 1 is fed by pipe 9B to the reactor 7 for oxidation of the nitrogen monoxide and from there by the pipe 6 at the same time as the nitrogen peroxide that has been made and regenerated, from whence it is introduced into the nitration circuit.

There is given below an example that illustrates the process of the invention used in the installation as described.

EXAMPLE

Nitration of an ethane-propane mixture is performed with nitrogen peroxide, in the presence of oxygen, with recycling of 2-nitropropane, also in the presence of an inert gas made up of carbon monoxide and carbon dioxide, and adjuvant. The pressure in the main nitration loop is 10 bars and the nitration temperature 332° C. with a contact time of 5.5 seconds.

Nitration is performed with recycling of the gases that have not reacted, recovery of the nitrogen monoxide, transformation into nitrogen peroxide and addition of nitrogen peroxide coming from a unit for oxidation of ammonia with oxygen, the oxygen addition being made up of oxygen introduced in excess required for oxidation of the nitrogen monoxide to nitrogen peroxide.

In this running of the installation of the nitration unit, there is a continuous purge of 20% of the amount of gas in the nitration loop. There is also a continuous addition of propane-ethane, 2-nitropropane, adjuvant, nitrogen peroxide and oxygen.

The weight compositions of the various constituents, reagents and effluents at the various points of the installation are given in the table below.

The compositions are designated by the following abbreviations: $C_2H_6$ ethane; $C_3H_8$ propane; $O_2$ oxygen; $NO_2$ nitrogen peroxide; $NO$ nitrogen monoxide; $NH_3$ ammonia; $CO$ carbon monoxide; $CO_2$ carbon dioxide; 2 $NC_3$ 2-nitropropane; $NC_1$ nitromethane; $NC_2$ nitroethane; 1 $NC_3$ 1-nitropropane. The running of the installation was followed and the compositions indicated for pipes 2B, 2C, 19, 24, 31, 8, 9 and 2A of the figure in the accompanying drawing and the amounts are given in kilograms.

TABLE

| Components | 2B | 2C | 19 | 24 | 31 | 8 | 9 | 2A |
|---|---|---|---|---|---|---|---|---|
| $C_2H_6$ | 1070 | 1000 | | 804 | 2.2 | | | 105 |
| $C_3H_8$ | 1181 | 917 | | 726 | 0.6 | | | 212 |
| $O_2$ | 92 | 0 | | | | 535 | | |
| $NO_2$ | 448 | 0 | | | | | | |
| $NO$ | 0 | 158 | | 37 | 0.4 | | | |
| $NH_3$ | 0 | | | | | | 107 | |
| $CO$ | 213 | 262 | | 213 | 44.8 | | | |
| $CO_2$ | 429 | 584 | | 429 | 5.5 | | | |
| 2 $NC_3$ | 133 | 171 | 165 | | | | | 133 |
| $NC_1$ | | 61 | 56 | | | | | |
| $NC_2$ | | 37 | 36 | | | | | |
| 1 $NC_3$ | | 22 | 21 | | | | | |
| adjuvant (Ethanal) | 7 | | | | | | | 7 |

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In a process for making nitroparaffins by continuous nitration in the homogeneous gaseous phase of a saturated hydrocarbon below $C_5$ using a nitrating agent, the improvement comprising:
   continuously adding said saturated gaseous hydrocarbon and nitrating agent to a closed nitration loop under pressure containing a nitrogen reactor, a reaction-heat thermal recovery and quenching unit downstream of said reactor, a separator unit downstream of said quenching unit for extraction from the gaseous phase of a condensed liquid phase containing the nitroparaffins produced, devices downstream of said separator unit for the purification of the gaseous phase and recovery of nitrogen monoxide, means for the separation of the purified gaseous phase into a major part and a minor part, and means for recycling said major part of said purified gaseous phase as part of said closed nitration loop back to said nitration reactor at the loop pressure;
   nitrating said saturated gaseous hydrocarbon in said nitrogen reactor of said closed nitration loop;
   separating the reaction effluents into a gaseous phase and a liquid phase in said closed nitration loop;
   purifying said gaseous phase in said closed nitration loop and recovering nitrogen monoxide therefrom;
   separating said gaseous phase into a major part and a minor part, and recycling said major part of said purified gaseous phase within said closed nitration loop back to said nitration reactor at the loop pressure;
   withdrawing said minor part of said gaseous phase as a continuous deconcentration purge from said closed nitration loop and recovering hydrocarbon therefrom; and
   withdrawing said liquid phase from said separator unit of said closed nitration loop and recovering nitroparaffin.

2. Process of making nitroparaffins according to claim 1, wherein the nitration loop pressure is between 1 bar and 30 bars.

3. Process making nitroparaffins according to claim 2, wherein the nitration is performed under a regular, progressive heat regime with an output temperature of effluents exiting said nitration reactor being below 400° C.

4. Process making nitroparaffins according to claim 2, wherein the saturated hydrocarbon below $C_5$ is ethane, propane or a mixture thereof.

5. Process of making nitroparaffins according to claims 1 or 2, wherein the nitrating agent is nitrogen peroxide, nitric acid, a mixture of nitrogen peroxide with nitric acid or any other agent carrying an easily transferable $NO$ or $NO_2$ group, or a mixture of nitric acid with another agent carrying an easily transferable $NO$ or $NO_2$ group.

6. Process of making nitroparaffins according to claims 1 or 2, wherein the nitration is performed in the presence of oxygen, a nitroparaffin such as 2-nitropropane or nitroethane or a mixture thereof, and an inert gas.

7. Process of making nitroparaffins according to claims 1 or 2, wherein said purification of the gaseous phase comprises at least a water treatment and a washing with a solution of metal sulfate, selected from iron, cobalt and copper sulfates.

8. Process of making nitroparaffins according to claim 1, wherein said minor portion of the gaseous phase, constituting the continuous deconcentration purge, is subjected under pressure to a secondary purification comprising a treatment with an aliphatic solvent of molecular mass between 100 and 200, then washing with a solution of metal sulfate selected from iron, cobalt and copper sulfate.

9. Process of making nitroparaffins according to claim 7, wherein the nitrogen monoxide recovered from the nitration loop is compressed to the nitration loop pressure, then oxidized to nitrogen peroxide and reintroduced into the nitration loop.

10. Process of making nitroparaffins according to claim 5, wherein the nitrating agent is nitrogen peroxide and wherein the nitrogen peroxide added comes from an oxidation of ammonia by oxygen; the nitrogen peroxide thus produced and the regenerated nitrogen monoxide being oxidized at the nitration loop pressure in the presence of excess oxygen, and the nitrogen peroxide formed being introduced to the nitration loop with excess oxygen.

11. Process of making nitroparaffins according to claim 1, wherein the nitration loop pressure is between 8 and 20 bars.

12. Process of making nitroparaffins according to claim 11, wherein said minor portion constituting said deconcentration purge constitutes about 10-20% of the amount of gas in the nitration loop.

* * * * *